United States Patent
Hagiwara et al.

(10) Patent No.: US 9,745,275 B2
(45) Date of Patent: Aug. 29, 2017

(54) PAIN-RELATED COMPOUND AND MEDICAL COMPOSITION

(71) Applicants: KYOTO UNIVERSITY, Kyoto-shi, Kyoto (JP); KAGOSHIMA UNIVERSITY, Kagoshima-shi, Kagoshima (JP)

(72) Inventors: Masatoshi Hagiwara, Kyoto (JP); Masayasu Toyomoto, Kyoto (JP); Takamitsu Hosoya, Tokyo (JP); Suguru Yoshida, Tokyo (JP); Takashi Kurihara, Kagoshima (JP)

(73) Assignees: KYOTO UNIVERSITY, Kyoto-Shi (JP); KAGOSHIMA UNIVERSITY, Kagoshima-Shi (JP)

( * ) Notice: Subject to any disclaimer, the term of this patent is extended or adjusted under 35 U.S.C. 154(b) by 0 days.

(21) Appl. No.: 15/105,985

(22) PCT Filed: Dec. 18, 2014

(86) PCT No.: PCT/JP2014/083569
§ 371 (c)(1),
(2) Date: Jun. 17, 2016

(87) PCT Pub. No.: WO2015/093567
PCT Pub. Date: Jun. 25, 2015

(65) Prior Publication Data
US 2017/0029389 A1     Feb. 2, 2017

(30) Foreign Application Priority Data
Dec. 18, 2013   (JP) ................ 2013-261396

(51) Int. Cl.
A61K 31/428   (2006.01)
C07D 277/64   (2006.01)

(52) U.S. Cl.
CPC ................ *C07D 277/64* (2013.01)

(58) Field of Classification Search
CPC .................... C07D 277/64; A61K 31/428
USPC ................. 548/180, 178; 514/367
See application file for complete search history.

(56) References Cited

U.S. PATENT DOCUMENTS 3,928,327 A    12/1975  Takamizawa et al.
2005/0113430 A1  5/2005  Tokai et al.
2005/0171026 A1  8/2005  Hagiwara et al.
2008/0255123 A1  10/2008  Meyer et al.
2011/0098284 A1  4/2011  Babul

FOREIGN PATENT DOCUMENTS

| JP | 50-89367 A | 7/1975 |
| JP | 2004-2352 A | 1/2004 |
| JP | 2008-539269 A | 11/2008 |
| WO | 2007/102861 A2 | 9/2007 |
| WO | WO 2009/085226 A2 | 7/2009 |
| WO | WO 2010/010797 A1 | 1/2010 |
| WO | WO 2013/168826 A1 | 11/2013 |

OTHER PUBLICATIONS

International Search Report for PCT/JP2014/083569 mailed on Mar. 17, 2015.
Kurihara et al., "Alleviation of behavioral hypersensitivity in mouse models of inflammatory pain with two structurally different casein kinase 1 (CK1) inhibitors", Molecular Pain 2014, 10 17/1-17/13, Mar. 10, 2014, total 13 pages.
Muraki et al., "Manipulation of Alternative Splicing by a Newly Developed Inhibitor of Clks", The Journal of Biological Chemistry, 2004, vol. 279, No. 23, pp. 24246-24254, total 13 pages.
Written Opinion of the International Searching Authority for PCT/JP2014/083569 (PCT/ISA/237) mailed on Mar. 17, 2015.
Extended European Search Report for corresponding European Application No. 14871323.3, dated May 3, 2017.

*Primary Examiner* — Charanjit Aulakh
(74) *Attorney, Agent, or Firm* — Birch, Stewart, Kolasch & Birch, LLP (57) ABSTRACT

Provided is a pain-related compound, a pain-related pharmaceutical composition, and use of the same. Provided in one or more embodiments is a compound represented by Formula (I), a prodrug of the same, or a pharmaceutically permissible salt of any of the same.

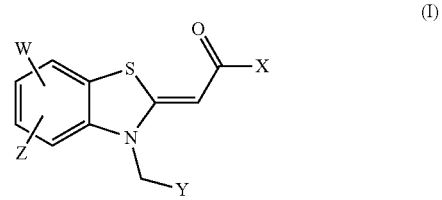

11 Claims, 8 Drawing Sheets

PAIN-RELATED COMPOUND AND MEDICAL COMPOSITION

TECHNICAL FIELD

The present disclosure relates to a pain-related compound, a pain-related pharmaceutical composition, and use of the same.

BACKGROUND ART

A medical condition of pain is a complicated physiological process that involves several kinds of sensory mechanisms and neural mechanisms. Pain can be defined as an unpleasant sensory or emotional experience accompanied by a real or potential tissue damage, or can be described as such a damage.

Pathophysiologically, pains can be classified into inflammatory pains and neuropathic pains.

The inflammatory pain is a nociceptive pain via nociceptor, which can be considered as a pain caused by an inflammatory mediator released to a site of tissue damage. The mechanism of an inflammatory pain is considered as follows. When a tissue is damaged and inflammation is caused, a pain producing substance such as bradykinin, ATP, or proton, and/or prostaglandin, serotonin, histamine, or an inflammatory cytokine are released, and a spontaneous pain develops incessantly. Further, hyperalgesia occurs due to hypersensitization of a nociceptor. Still further, as a mechanism of hypersensitization of a nociceptor, the phosphorylation of an ion channel, particularly TRPV1channel known as a capsaicin receptor, is reported.

On the other hand, a neuropathic pain can be defined as a pain that is caused by a lesion or a disease of a somatosensory nervous system (International Association for the Study of Pain in 2011). In Japan, it is estimated that there are several millions of neuropathic pain patients. The pain is a pain that does not involve excitation of a nociceptor, and that involves plastic changes of peripheral nerves or central nerves. As a mechanism of development of a neuropathic pain, the following have been reported: the ectopic firing of peripheral nerves; the neuroanatomical reconstruction in peripheral nerves and dorsal horns of the spinal cord; the control of descending inhibition systems; and the activation of glial cells in the spinal cord.

Several documents including Patent Document 1 disclose methods and compositions for treating pains. Further, Patent Document 2 discloses a pharmaceutical composition for suppressing abnormal splicing that occurs when kinase is over-induced.

PRIOR ART DOCUMENT

Patent Document

[Patent Document 1] JP-T-2008-539269
[Patent Document 2] US Patent Application Publication No. 2005/0171026

SUMMARY OF THE INVENTION

Problem to be Solved by the Invention

The present disclosure, in one aspect, provides a pain-related compound, a pain-related pharmaceutical composition, and the use of the same.

Means for Solving the Problem

The present disclosure, in one or more embodiments, relates to a compound represented by Formula (I) below, a prodrug of the same, or pharmaceutically permissible salts of any of the same.

where W, X, Y, and Z each independently represent a hydrogen atom, a halogen atom, a substituted or unsubstituted amino group, an azido group, a cyano group, a nitro group, a hydroxyl group, a straight or branched chain or cyclic alkyloxy group having one to six carbon atoms, a substituted or unsubstituted aryloxy group, a substituted or unsubstituted heteroaryloxy group, a mercapto group, a straight or branched chain or cyclic alkylthio group having one to six carbon atoms, a substituted or unsubstituted arylthio group, a substituted or unsubstituted heteroarylthio group, a straight or branched chain or cyclic alkyl group having one to six carbon atoms, a benzyl or heteroatylmethyl group, a substituted or unsubstituted aryl group, or a substituted or unsubstituted heteroaryl group.

The present disclosure, in one or more embodiments, relates to a pharmaceutical composition that contains, as an active ingredient, the compound represented by Formula (I) according to the present disclosure, the prodrug of the same, or the pharmaceutically permissible salt of any of the same.

The present disclosure, in one or more embodiments, relates to use of the compound represented by Formula (I) according to the present disclosure, the prodrug of the same, or the pharmaceutically permissible salt of any of the same, for producing the pharmaceutical composition according to present disclosure.

The present disclosure, in one or more embodiments, relates to a method for reducing pain, suppressing the exacerbation of pain, and/or treating pain, the method including administering the pharmaceutical composition according to the present disclosure to a target that requires the administration of the pharmaceutical composition. Further, the present disclosure, in one or more embodiments, relates to use of the compound represented by Formula (I) according to the present disclosure, the prodrug of the same, or the pharmaceutically permissible salt of any of the same, or to use of the pharmaceutical composition according to the present disclosure, in a method for reducing pain, for suppressing the exacerbation of pain, and/or for treating pain, the method including administering the pharmaceutical composition according to the present disclosure to a target that requires the administration of the pharmaceutical composition.

MODE FOR CARRYING OUT THE INVENTION

[Compound Represented by General Formula (I)]

The present disclosure, in one aspect, relates to a compound represented by Formula (I) below, a prodrug of the same, or a pharmaceutically permissible salt of any of the same.

(I)

In Formula (I), W, X, Y, and Z each independently represent a hydrogen atom, a halogen atom, a substituted or unsubstituted amino group, an azido group, a cyano group, a nitro group, a hydroxyl group, a substituted or unsubstituted straight or branched chain or cyclic alkyloxy group having one to six carbon atoms, a substituted or unsubstituted aryloxy group, a substituted or unsubstituted heteroaryloxy group, a mercapto group, a straight or branched chain or cyclic alkylthio group having one to six carbon atoms, a substituted or unsubstituted arylthio group, a substituted or unsubstituted heteroarylthio group, a substituted or unsubstituted straight or branched chain or cyclic alkyl group having one to six carbon atoms, a benzyl or heteroarylmethyl group, a substituted or unsubstituted aryl group, or a substituted or unsubstituted heteroaryl group.

Examples of the straight or branched chain alkyl group having one to six carbon atoms in W, X, Y, and Z, in one or more embodiments, include methyl group, ethyl group, 1-propyl group, 2-propyl group, 2-methyl-1-propyl group, 2-methyl-2-propyl group, 1-butyl group, 2-butyl group, 1-pentyl group, 2-pentyl group, 3-pentyl group, 2-methyl-1-butyl group, 3-methyl-1-butyl group, 2-methyl-2-butyl group, 3-methyl-2-butyl group, 2,2-dimethyl-1-propyl group, 1-hexyl group, 2-hexyl group, 3-hexyl group, 2-methyl-1-pentyl group, 3-methyl-1-pentyl group, 4-methyl-1-pentyl group, 2-methyl-2-pentyl group, 3-methyl-2-pentyl group, 4-methyl-2-pentyl group, 2-methyl-3-pentyl group, 3-methyl-3-pentyl group, 2,3-dimethyl-1-butyl group, 3,3-dimethyl-1-butyl group, 2,2-dimethyl-1-butyl group, 2-ethyl-1-butyl group, 3,3-dimethyl-2-butyl group, and 2,3-dimethyl-2-butyl group. Further, examples of the cyclic alkyl group having one to six carbon atoms in W, X, Y, and Z, in one or more embodiments, include cyclo propyl, cyclo butyl, cyclo pentyl, and cyclo hexyl.

Examples of heteroaryl (including heteroaryl in the heteroarylmethyl group) in W, X, Y, and Z, in one or more embodiments, include a five- or six-membered monocyclic group having one to two nitrogen atoms, a five- or six-membered monocyclic group having one to two nitrogen atoms, and one oxygen atom or one sulfur atom, a five-membered monocycle group having one oxygen atom or one sulfur atom, and a bicyclic group having one to four nitrogen atoms obtained by condensation of a six-membered ring and a five- or six-membered ring. Further, in another one or more embodiments, examples of the same include 2-piridyl, 3-piridyl, 4-piridyl, 2-thienyl, 3-thienyl, 3-oxadiazolyl, 2-imidazolyl, 2-thiazolyl, 3-isothiazolyl, 2-oxazolyl, 3-isoxazolyl, 2-furyl, 3-furyl, 3-pyrrolyl, 2-quinolyl, 8-quinolyl, 2-quinazolinyl, and 8-prenyl. Examples of the aryl group in $R^1$ and $R^2$ include an aryl group having ten or less carbon atoms such as a phenyl group, or a naphthyl group The substituent in W, X, Y, and Z may be one substituent, or a plurality of identical or different substituents, and in one or more embodiments, examples of the same include a halogen atom, a cyano group, a trifluoro methyl group, a nitro group, a hydroxyl group, a methyleneclioxy group, a lower alkyl group, a lower alkoxy group, a benzyloxy group, a lower alkanoyloxy group, an amino group, a mono-lower alkylamino group, a di-lower alkylamino group, a carbamoyl group, a lower alkylaminocarbonyl group, a di-lower alkylaminocarbonyl group, a carboxyl group, a lower alkoxycarbonyl group, a lower alkylthio group, a lower alkylsulfinyl group, a lower alkylsulfonyl group, a lower alkanolyamino group, and a lower alkyl sulfonamide group. In the present disclosure, in one or more embodiments, examples of the halogen atom include atoms such as fluorine, chlorine, bromine, and iodine. Further, in the present disclosure, in one or more embodiments, the lower alkyl is a straight or branched chain alkyl group having one to six carbon atoms.

In one or more non-limited embodiments, the compound represented by Formula (I) is a compound represented by Formula (II) below.

(II)

In Formula (II), $X_1$ and $Y_1$ each independently represent a halogen atom, or a substituted or unsubstituted straight or branched chain or cyclic alkyl group having one to six carbon atoms, and $Z_1$ and $W_1$ each independently represent a hydrogen atom, a halogen atom, a hydroxyl group, a straight or branched chain or cyclic alkyloxy group having one to six carbon atoms, or a substituted or unsubstituted straight or branched chain or cyclic alkyl group having one to six carbon atoms. Examples of the substituent in $X_1$, $Y_1$, $Z_1$ and $W_1$ include the substituents mentioned above.

In the compound represented by Formula (II), in one or more embodiments, $X_1$ and $Y_1$ each represent an alkyl group having 1 to 4 carbon atoms, $Z_1$ represents a halogen atom, a hydroxyl group, or an alkyloxy group having 1 to 4 carbon atoms, and $W_1$ represents a hydrogen atom.

Examples of the compound represented by Formula (I) or (II), as one or more non-limited embodiments, include compounds indicated below.

-continued and

Further, the compounds represented by Formulae (I) and (II), in cases where an asymmetric carbon atom is present and/or a stereoisomer is present, are mixed isomers or isolated isomers, in one or more embodiments.

In the present disclosure, examples of the "prodrug", in one or more embodiments, include those which can be easily hydrolyzed in vivo so that the compound represented by Formula (I) can be reproduced. In a case where the compound represented by Formula (I) is, for example, a compound having a carboxyl group, the prodrug is, for example, the compound in which the carboxyl group has become an alkoxycarbonyl group, the compound in which the carboxyl group has become an alkylthio carbonyl group, or the compound in which the carboxyl group has become an alkylaminocarbonyl group. Further, in a case where the compound represented by Formula (I) is, for example, a compound having an amino group, the prodrug is, for example, the compound in which the amino group is substituted with an alkanoly group, thereby becoming an alkanolyamino group, the compound in which the amino group is substituted with an alkoxycarbonyl group, thereby becoming an alkoxycarbonyl amino group, the compound in which the amino group has become an acyloxymethylamino group, or the compound in which the amino group has become hydroxylamine. Still further, in a case where the compound represented by Formula (I) is, for example, a compound having a hydroxyl group, the prodrug is, for example, the compound in which the hydroxyl group is substituted with an acyl group, thereby becoming an acyloxy group, the compound in which the hydroxyl group has become a phosphoric acid ester, the compound in which the hydroxyl group has become an acyloxymethyloxy group. The alkyl part of the group used in the prodrug conversion in these cases is, for example, the above-described alkyl group, and the alkyl group may be substituted (with, for example, an alkoxy group having one to six carbon atoms).

In one or more embodiments, in a case of, for example, the compound in which the carboxyl group has become an alkoxycarbonyl group, the alkyl part is a lower alkoxycarbonyl (for example, having one to six carbon atoms) such as methoxycarbonyl or ethoxycarbonyl, or a lower alkoxycarbonyl (for example, having one to six carbon atoms) by substitution with an alkoxy group, such as methoxymethoxycarbonyl, ethoxymethoxycarbonyl, 2-methoxyethoxycarbonyl, 2-methoxyethoxymethoxycarbonyl, or pivaloyloxymethoxycarbonyl.

In the present disclosure, the "pharmaceutically permissible salt" encompasses pharmaceutically, pharmacologically, and/or medically permissible salts, and examples of the same include inorganic acid salts, organic acid salts, inorganic base salts, organic base salts, and acidic or basic amino acid salts.

Preferable examples of the inorganic acid salt include hydrochlorides, hydrobromic acid salts, sulfuric acid salts, nitric acid salts, and phosphoric acid salts. Preferable examples of the organic acid salt include acetic acid salts, succinic acid salts, fumaric acid salts, maleic acid salts, tartaric acid salts, citric acid salts, lactic acid salts, stearic acid salts, benzoic acid salts, methanesulfonic acid salts, and p-toluenesulfonic acid salts.

Preferable examples of the above-described inorganic base salt include alkali metal salts such as sodium salts and potassium salts, alkali earth metal salts such as calcium salts and magnesium salts, aluminum salts, and ammonium salts. Preferable examples of the above-described organic base salt include diethylamine salts, diethanolamine salts, meglumine salts, and N,N-dibenzylethylenediamine salts.

Preferable examples of the above-described acidic amino acid salt include aspartic acid salts, and glutamic acid salts. Preferable examples of the basic amino acid salt include arginine salts, lysine salts, and ornithine salts.

The "salt of the compound" in the present disclosure can encompass a hydrate formed with the compound when the compound is left to stand in the atmosphere thereby absorbing moisture. Further, in the present disclosure, the "salt of the compound" can also encompass a solvate formed with the compound when the compound absorbs another certain type of a solvent.

[Pharmaceutical Composition]

The present disclosure, in one aspect, relates to a pharmaceutical composition that contains, as an active ingredient, the compound represented by Formula (I), the prodrug of the same, or the pharmaceutically permissible salt of any of the same.

The compound represented by Formula (I) or the pharmaceutical composition according to the present disclosure, in one or more embodiments, can be used for the purpose of reducing pain, suppressing the exacerbation of pain, and/or treating pain. Further, the compound represented by Formula (I) or the pharmaceutical composition according to the present disclosure, in one or more other embodiments, can be used for the purpose of analgesia. The analgesia encompasses killing pain. Details of the mechanism in which the compound represented by Formula (I) or the pharmaceutical composition according to the present disclosure can be used for the purpose of reducing pain, suppressing the exacerbation of pain, and/or treating pain, as well as for the purpose of analgesia are not clear, but it can be presumed that the compound represented by Formula (I) exerts analgesic actions via an opioid receptor, in one or more embodiments. The present disclosure and the present invention, however, do not have to be limited to this mechanism.

The "pain" in the present disclosure, in one or more embodiments, refers to an inflammatory pain or a neuropathic pain classified pathophysiologically. Further, in the present disclosure, in one or more embodiments, the "pain" refers to an acute pain, an inflammatory pain, a visceralgia, a breakthrough pain, a nociceptive pain, a neuropathic pain, a chronic pain, or a cancer-related pain, which are classified depending on the time lapse or the mechanism The "pharmaceutical composition" in the present disclosure, in one or more embodiments, can be in a dosage form suitable for administration, obtained by applying a known formulation technology The administration form is, for example, oral administration in a dosage form such as a tablet agent, a capsule agent, a granule agent, a powder agent, a pill agent, a troche agent, a syrup agent, of a liquid agent, though the dosage form is not limited to these. Alternatively, the administration form is, for example, non-oral administration in a dosage form such as an injection agent, a liquid agent, an aerosol agent, a suppository agent, a plaster agent, a poultice agent, a lotion agent, a liniment agent, an ointment agent, or an eye drop agent. These formulations can be produced by a known method using an additive agent such as an excipient, a lubricant, a binder, a disintegrator, a stabilizer, a flavoring agent, and a diluent, though the additive agent is not limited to these.

The pharmaceutical composition according to the present disclosure, in one or more embodiments, does not contain another active ingredient having therapeutic (or analgesic) effects, or alternatively, further contains one or more active ingredients.

Examples of the above-described excipient include: starches such as starch, potato starch, and corn starch; lactose; crystalline cellulose; and phosphoric acid hydrogen calcium, though the excipient is not limited to these. Examples of the above-described coating agent include ethyl cellulose, hydroxypropyl cellulose, hydroxypropyl methyl cellulose, shellac, talc, carnauba wax, and paraffin, though the coating agent is not limited to these. Examples of the above-described binder include polyvinylpyrrolidone, macrogol, and the same compounds as those mentioned as the examples of the excipient, though the binder is not limited to these. Examples of the above-described disintegrator include the same compounds as those mentioned as the examples of the excipient, as well as chemically modified starches and celluloses such as croscarmellose sodium, carboxymethyl starch sodium, and cross-linked polyvinylpyrrolidone, though the disintegrator is not limited to these. Examples of the above-described stabilizer include: paraoxybenzoic acid esters such as methylparaben and propylparaben; alcohols such as chlorobutanol, benzyl alcohol, phenyl ethyl alcohol; benzalkonium chloride; phenols such as phenol, and cresol; thimerosal; dehydroacetic acid; and sorbic acid, though the stabilizer is not limited to these. Examples of the above-described flavoring agent include sweeteners, acidifiers, and aromas that are typically used, though the flavoring agent is not limited to these.

Further, in the production of a liquid agent, ethanol, phenol, chlorocresol, purification water, distilled water or the like can be used as a solvent, though the solvent is not limited to these. Besides, a surfactant, an emulsifier, and the like also can be used as required. Examples of the foregoing surfactant and emulsifier include polysorbate 80, polyoxyl stearate 40, and lauromacrogol, though the surfactant and the emulsifier are not limited to these.

The method for using the pharmaceutical composition according to the present disclosure can vary with the symptom, the age, the administering method, and the like. The using method, in one or more embodiments, can be a method of intermittently or continuously administering the compound represented by Formula (I) as an active ingredient, orally, percutaneously, submucosally, subcutaneously, intramuscularly, intravascularly, intracerebrally, or intraperitoneally in such a manner that the concentration in the body is in a range of 100 nM to 1 mM, though the method is not limited to these. For example, in one or more non-limited embodiments, in a case of oral administration, the method is such a method of administration to a target (an adult if the target is a human) in an amount from a lower limit of 0.01 mg or 0.1 mg, to an upper limit of 2000 mg, 500 mg, or 100 mg in terms of the compound represented by Formula (I), per one day, in one does, or divided into several doses, according to the symptom. In one or more non-limited embodiments, for example, in a case of intravenous administration, the method is such a method of administration to a target (an adult if the target is a human) in an amount from a lower limit of 0.001 mg, or preferably 0.01 mg, to an upper limit of 500 mg, or 50 mg per one day, in one dose, or divided into several doses, according to the symptom.

[Method and Use]

The present disclosure, in one aspect, relates to a method for reducing pain, suppressing the exacerbation of pain, and/or treating pain, the method including administering the pharmaceutical composition according to the present disclosure to a target that requires the administration of the pharmaceutical composition. In one or more embodiments, the target is, for example, a mammal, a mammal other than a human, or a human; or alternatively, a mammal, a mammal other than a human, or a human that exhibits a symptom of a pain. The method for administering the pharmaceutical composition according to the present disclosure, in one or more embodiments, may conform to the above-described method for using the pharmaceutical composition.

The present disclosure, therefore, can further relate to one or more embodiments described below.

[A1] A compound represented by Formula (I) below, a prodrug of the same, or a pharmaceutically permissible salt of any of the same:

(I)

where W, X, Y, and Z each independently represent a hydrogen atom, a halogen atom, a substituted or unsubstituted amino group, an azido group, a cyano group, a nitro group, a hydroxyl group, a straight or branched chain or cyclic alkyloxy group having one to six carbon atoms, a substituted or unsubstituted aryloxy group, a substituted or unsubstituted heteroaryloxy group, a mercapto group, a straight or branched chain or cyclic alkylthio group having one to six carbon atoms, a substituted or unsubstituted arylthio group, a substituted or unsubstituted heteroarylthio group, a straight or branched chain or cyclic alkyl group having one to six carbon atoms, a benzyl or heteroarylmethyl group, a substituted or unsubstituted aryl group, or a substituted or unsubstituted heteroaryl group.

[A2] A compound represented by Formula (II) below, a prodrug of the same, or a pharmaceutically permissible salt of any of the same:

(II)

where

$X_1$ and $Y_1$ each independently represent a halogen atom, or a substituted or unsubstituted straight or branched chain or cyclic alkyl group having one to six carbon atoms, and

$Z_1$ and $W_1$ each independently represent a hydrogen atom, a halogen atom, a hydroxyl group, a straight or branched chain or cyclic alkyloxy group having one to six carbon atoms, or a substituted or unsubstituted straight or branched chain or cyclic alkyl group having one to six carbon atoms.

[A3] A pharmaceutical composition containing, as an active ingredient, the compound according to [A1] or [A2], the prodrug of the same, or the pharmaceutically permissible salt of any of the same.

[A4] The pharmaceutical composition according to [A3], for reducing pain, suppressing the exacerbation of pain, and/or treating pain.

[A5] A pharmaceutical composition for reducing pain, suppressing the exacerbation of pain, and/or treating pain, the pharmaceutical composition containing, as an active ingredient, a compound represented by any one of chemical formulae below, a prodrug of the same, or a pharmaceutically permissible salt of any of the same:

and

[A6] The pharmaceutical composition according to [A4] or [A5], wherein the pain is an inflammatory pain and/or a neuropathic pain.

[A7] The pharmaceutical composition according to any one of [A3] to [A6], for an analgesic action via an opioid receptor.

[A8] Use of the compound according to [A1] or [2], the prodrug of the same, or the pharmaceutically permissible salt of any of the same, for producing the pharmaceutical composition according to any one of [A3] to [A7].

[A9] Use of the compound according to [A1] or [2], the prodrug of the same, the pharmaceutically permissible salt of any of the same, in a method for reducing pain, suppressing the exacerbation of pain, and/or treating pain, the method including administering the pharmaceutical composition according to any one of [A3] to [A7] to a target that requires lives the administration of the pharmaceutical composition; or a method of administering the pharmaceutical composition according to any one of [A3] to [A7] to a target that requires the administration of the pharmaceutical composition.

[A10] A method for reducing pain, suppressing the exacerbation of pain, or treating pain, the method comprising administering the pharmaceutical composition according to any one of [A3] to [A7] to a target that requires the administration of the pharmaceutical composition.

EXAMPLE

The following description describes the present disclosure in more details by way of examples. These examples however are merely illustrative, and the present disclosure is not limited to these examples. The entirety of the documents cited in the present disclosure is incorporated in the present disclosure.

Production Example 1

Production of Compound 1

Compound 1

The compound 1 was synthesized in the following manner.

Ethyl iodide (iodoethane) (50.0 mL, 622 mmol, commercial product) solution of 5-fluoro-2-methylbenzothiazole (48.8 g, 292 mmol, commercial product) was heated and refluxed (oil bath temperature 100° C.) for 72 hours. After the solution was cooled at room temperature, a colorless solid substance formed was collected by filtration, washed with ethyl acetate, and dried under a reduced pressure, whereby 3-ethyl-5-fluoro-2-methylbenzothiazolium iodide (46.5 g, 151 mmol, 51.7%) was obtained in a colorless solid state.

Next, in an argon atmosphere, acetic anhydride (22.5 mL, 236 mmol, commercial product) and triethylamine (32.2 mL, 231 mmol, commercial product) were added sequentially to an acetonitrile solution (150 mL) of 3-ethyl-5-fluoro-2-methylbenzothiazolium iodide (32.3 g, 100 mmol) at room temperature, and thereafter, this was heated and refluxed (oil bath temperature 80° C.) for three hours. After the reaction mixture thus obtained was cooled at room temperature, water was added thereto, and the reaction mixture was extracted with ethyl acetate (×3). This was washed with a saturated saline solution, and thereafter, was dried with anhydrous sodium sulfate. After this was filtered, a filtrate thus obtained was concentrated under a reduced pressure. The obtained crude reaction product was purified by silica gel column chromatography (Wako Pure Chemical Industries, Ltd., Presep (trademark) Silica Gel (HC-N) Type2L, hexane/ethyl acetate=5/1 to 1/1), and thereafter, recrystallized with hexane-ethyl acetate. Thus, (1Z)-1-(3-ethyl-5-fluoro-2(3H)-benzothiazolylidene)-2-propanone (17.8 g, 75.2 mmol, 75.2%) (Compound 1) was obtained in a colorless needle crystal form. Melting point, 179-180° C.; TLC Rf 0.36 (hexane/ethyl acetate=7/3); $^1$H NMR (CDCl$_3$, 400 MHz) δ 1.38 (t, 3H, J=7.2 Hz), 2.25 (s, 3H),4.01 (q, 2H, J=7.2 Hz), 5.90 (s, 1 H), 6.82 (dd, 1H, J=2.4, 9.6Hz), 6.88 (ddd, 1H, J=2.4, 8.4, 8.4 Hz), 7.48 (dd, 1H, J=5.2, 8.4 Hz); IR (KBr, cm$^{-1}$) 978, 1042, 1125, 1192, 1326, 1332, 1354, 1382, 1449, 1453, 1468, 1488, 1492, 1604, 2981.

Production Example 2

Production of Compound 2

Compound 2

The compound 2 was synthesized according to the technique disclosed in the following document (M. Muraki, et al., Manipulation of Alternative Splicing by a Newly Developed Inhibitor of Clks, The Journal of Biological Chemistry, 2004, 279, 24246-24254, or WO 2010010797 A1).

Production Example 3

Production of Compound 3

Compound 3

The compound 3 was synthesized in the following manner.

Ethyl iodide (iodoethane) (2.00 mL, 24.6 mmol, commercial product) solution of 6-methoxy-2-methylbenzothiazole (201 mg, 1.12 mmol, commercial product) was heated and refluxed (oil bath temperature 100° C.) for 24 hours. After the solution was cooled at room temperature, a colorless solid substance formed was collected by filtration, washed with ethyl acetate, and dried under a reduced pressure, whereby 3-ethyl-6-methoxy-2-methylbenzothiazolium iodide (257 mg, 0.766 mmol, 68.4%) was obtained in a colorless solid state.

In an argon atmosphere, acetic anhydride (0.170 mL, 1.80 mmol, commercial product), and triethylamine (0.250 mL, 1.79 mmol, commercial product) were added sequentially to an acetonitrile solution (2 mL) of 3-ethyl-6-methoxy-2-methylbenzothiazolium iodide (257 mg, 0.766 mmol) at room temperature, and thereafter, this was heated and refluxed (oil bath temperature 80° C.) for two hours. After the reaction mixture thus obtained was cooled at room temperature, this reaction mixture was concentrated under a reduced pressure, water was added thereto, and the reaction mixture was extracted with ethyl acetate (×3). This was washed with a saturated saline solution, and thereafter, was dried with anhydrous sodium sulfate. After this was filtrated, a filtrate thus obtained was concentrated under a reduced pressure. The obtained crude reaction product was purified by silica gel column chromatography (hexane/ethyl acetate =1/2), and (1Z)-1-(3-ethyl-6-methoxy-2(3H)-benzothiazoylidene)-2-propanone (115 mg, 0.461 mmol, 60.2%) (Compound 3) was obtained in a light yellow solid state. Melting point 134-135° C. ; TLC Rf 0.27 (hexane/ethyl acetate=1/2); $^1$H NMR (CDCl$_3$, 400 MHz) δ 1.36 (t, 3H, J=7.2 Hz), 2.23 (s, 3H), 4.03 (q, 2H, J=7.2 Hz), 5.82 (s, 1 H), 6.91 (dd, 1H, J=2.5, 8.7 Hz), 7.01 (d,1H, J=8.7 Hz), 7.13 (d, 1H, J=2.5 Hz); IR (KBr, cm$^{-1}$) 720, 760, 801, 959, 1020, 1046, 1136, 1188, 1219, 1258, 1273, 1298, 1327, 1358, 1472, 1487, 1590, 1603, 2342, 2361, 2980.

Production Example 5

Production of Compound 5

Compound 5

The compound 5 was synthesized in the following manner.

Ethyl iodide (iodoethane) (3.70 mL, 46.3 mmol, commercial product) solution of 5-bromo-2-methylbenzothiazole (5.11 g, 22.4 mmol, commercial product) was heated and refluxed (oil bath temperature 100° C.) for 72 hours. After the solution was cooled at room temperature, a colorless solid substance formed was collected by filtration, washed with ethyl acetate, and dried under a reduced pressure, whereby 5-bromo-3-ethyl-2-methylbenzothiazolium iodide) (4.11 g, 10.7 mmol, 47.7%) was obtained in a colorless solid state.

Next, in an argon atmosphere, acetic anhydride (2.41 mL, 25.5 mmol, commercial product) and triethylamine (3.44 mL, 247 mmol, commercial product) were added sequentially to an acetonitrile (18 mL) solution of 5-bromo-3-ethyl-2-methylbenzothiazolium iodide (4.10 g, 10.7 mmol) at room temperature, and thereafter, this was heated and refluxed (oil bath temperature 80° C.) temperature, 300 mL of methyl chloride was added to this reaction mixture. This was washed with an aqueous solution of ammonium chloride and a saturated saline solution sequentially, and was dried with anhydrous sodium sulfate. After this was filtered, a filtrate thus obtained was concentrated under a reduced pressure. The obtained crude reaction product was purified by silica gel column chromatography (Wako Pure Chemical Industries, Ltd., Presep (trademark) Silica Gel (HC-N) Type L, hexane/ethyl acetate=5/1 to 1/2), and thereafter, recrystallized with hexane-ethyl acetate. Thus, (1Z)-1-(5-bromo-3-ethyl-2(3H)-benzothiazoylidene)-2-propanone (2.72 g, 9.13 mmol, 85.3%) (Compound 5) was obtained in a colorless solid state. Melting point 184-185° C.; TLC Rf 0.39 (hexane/ethyl acetate=7/3); $^1$H NMR (CDCl$_3$, 400 MHz) δ1.38 (t, 3H, J=7.2 Hz), 2.25 (s, 3H), 4.02 (q, 2H, J=7.2 Hz), 5.90 (s, 1 H), 7.22 (d, 1H, J=1.6 Hz), 7.27 (dd, 1H, J=1.6, 8.4Hz), 7.41 (d, 1H, J=8.4 Hz); IR (KBr, cm$^{-1}$) 800, 850, 964, 1086, 1139, 1188, 1299, 1328, 1353, 1382, 1450, 1467, 1489, 1588, 1614, 2978.

Production Example 6

Production of Compound 6

Compound 6

The compound 6 was synthesized in the following manner.

Ethyl iodide (iodoethane) (9.10 mL, 114 mmol, commercial product) solution of 5-chloro-2-methylbenzothiazole) (10.0g, 54.3 mmol, commercial product) was heated and refluxed (oil bath temperature 100° C.) for 72 hours. After the solution was cooled washed with ethyl acetate, and dried under a reduced pressure, whereby 5-chloro-3-ethyl-2-methylbenzothiazolium iodide (9.96 g, 29.3 mmol, 53.9%) was obtained in a colorless solid state.

Next, in an argon atmosphere, acetic anhydride (3.29 mL, 34.8 mmol, commercial product) and triethylamine (4.70 mL, 33.8 mmol, commercial product) were added sequentially to an acetonitrile (25 mL) solution of 5-chloro-3-ethyl-2-methylbenzothiazolium iodide (4.95 g, 14.6 mmol) at room temperature, and thereafter, this was heated and refluxed (oil bath temperature 80° C.) for three hours. After the reaction mixture thus obtained was cooled at room temperature, 300 mL of methyl chloride was added to this reaction mixture. This was washed with an aqueous solution of ammonium chloride and a saturated saline solution sequentially, and was dried with anhydrous sodium sulfate. After this was filtered, a filtrate thus obtained was concentrated under a reduced pressure. The obtained crude reaction product was purified by silica gel column chromatography (Wako Pure Chemical Industries, Ltd., Presep (trademark) Silica Gel (HC-N) Type L, hexane/ethyl acetate=5/1 to 1/2), and thereafter, recrystallized with hexane-ethyl acetate. Thus, (1Z)-1-(5-chloro-3-ethyl-2(3H)-benzothiazoylidene) propan-2-one (3.42 g, 75.2 mmol, 92.2%) (Compound 6) was obtained in a colorless solid state. Melting point 175-176° C.; TLC Rf 0.43 (hexane/ethyl acetate=7/3); $^1$H NMR (CDCl$_3$, 400 MHz) 6 1.38 (t, 3H, J=7.2 Hz), 2.25 (s, 3H), 4.02 (q, 2H, J=7.2 Hz), 5.90 (s, 1 H), 7.07 (d, 1H, J=1.6 Hz), 7.13 (dd, 1H, J=1.6, 8.4 Hz), 7.47 (d, 1H, J=8.4 Hz); IR (KBr, cm$^{-1}$) 839, 938, 963, 1044, 1088, 1140, 1189, 1297, 1314, 1328, 1353, 1382, 1463, 1492, 1582, 1613, 2979.

Experiment Example 1

After subcutaneous plantar administration of carrageenan, acute inflammation develops over several hours, which causes a phenomenon of hypersensitivity to mechanical stimulation and thermal stimulation. A therapeutic agent containing the compound 1 as an active ingredient was administered to each of model mice of this carrageenan-induced inflammatory pain, and pain was evaluated.

More specifically, at seven hours after carrageenan was subcutaneously administered to a hind limb sole of each mouse (male, C57BL/6J, 6 to 8 weeks old), the compound 1 was administered orally, and at one hour after the administration of the compound 1, therapeutic effects thereof with respect to mechanical allodynia were determined. Specific conditions are as follows.

Mouse: C57BL/6J, male, 8 weeks old, n =4 (each foot, n=8) Induction of pain: 25 μL of physiological saline solution containing 2% of λ-carrageenan was injected subcutaneously to hind limb soles, so that pain was induced.

Administration of therapeutic agent: Solution of the compound 1, 0.2 ml per 20 g of the body weight of each mouse, was administered orally, so that 1 nmol of the compound 1 was administered per 1 g of the body weight of the mouse. The solution of the compound 1 was prepared by dissolving the compound 1 in 99% DMSO and diluting the same with physiological saline solution (0.2% DMSO in physiological saline solution).

Evaluation of pain: Evaluation was performed by von Frey test. More specifically, a hind limb sole of the mouse was mechanically stimulated with tips of von-Frey filaments having a variety of thicknesses, and a load of stimulation at which the mouse initiated a withdrawal behavior was determined. The results are illustrated in FIG. 1.

Figure 1:
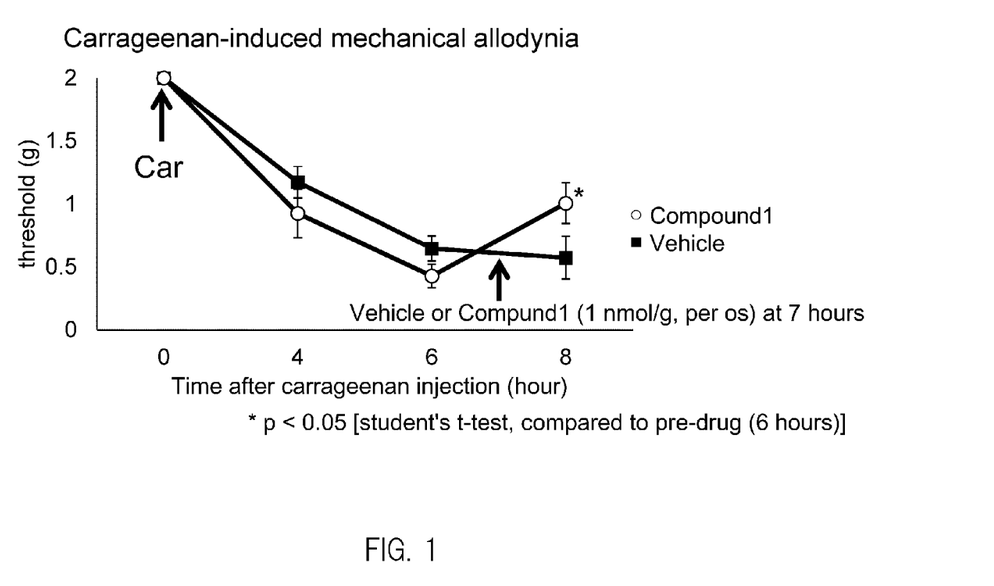
FIG. 1 is an exemplary graph illustrating effects of pain therapy with a compound 1 of carrageenan-induced inflammatory pain model mice. The compound 1 was administered orally, and therapeutic effects with respect to mechanical allodynia (pain from mechanical stimulation) were evaluated. The longitudinal axis of the graph indicates threshold (load) of a withdrawal reflex behavior to mechanical stimulation with von-Frey filaments.

As illustrated in FIG. 1, with the compound 1 administered, pain was significantly reduced. On the other hand, regarding the example to which DMSO was used in place of the compound 1, the reduction of pain by the administration of the same was not observed.

Experiment Example 2

Before and after carrageenan (2%, 25 μl) was subcutaneously administered to a one-side hind limb sole of each mouse (male, C57BL/6J, (to 8 weeks old), thermal stimulation was applied, and latency of a withdrawal reflex behavior of the hind limb was measured. The appearance of the phenomenon of thermal hyperalgesia due to carrageenan was checked over six hours after the administration, and thereafter, the compound 1 or a solvent used for dissolution (veh.) was administered orally (1 pmol or 10 pmol per 1 g of the mouse body). Effects were examined over two hours thereafter. The results are illustrated in FIG. 2.

Figure 2:
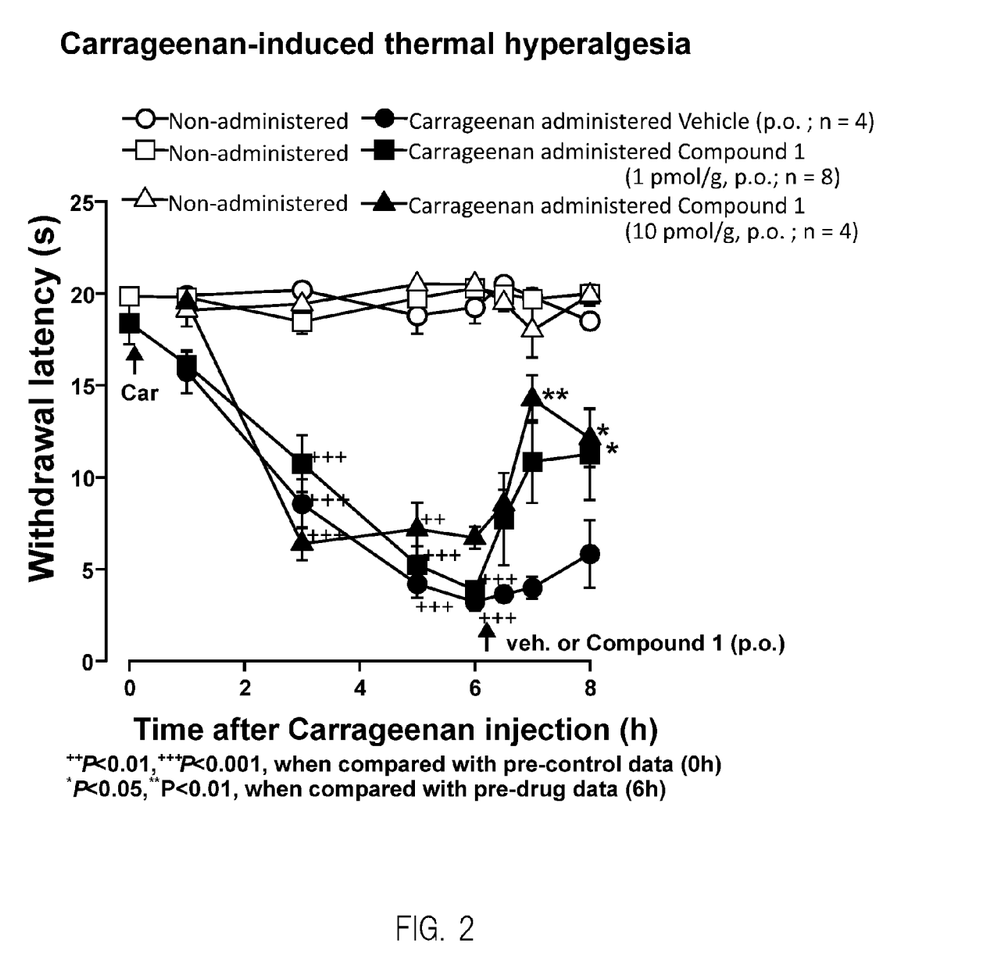
FIG. 2 is an exemplary graph illustrating effects of pain therapy with a compound 1 of carrageenan-induced inflammatory pain model mice. The compound 1 was administered orally, and therapeutic effects with respect to thermal hyperesthesia (pain from thermal stimulation) were evaluated. The longitudinal axis of the graph indicates latency (time) until a withdrawal reflex behavior to thermal stimulation.

As illustrated in FIG. 2, pain was significantly reduced by the administration of the compound 1. On the other hand, in the examples with use of DMSO in place of the compound 1, any reduction of pain by the administration was not observed.

Experiment Example 3

Figure 3:
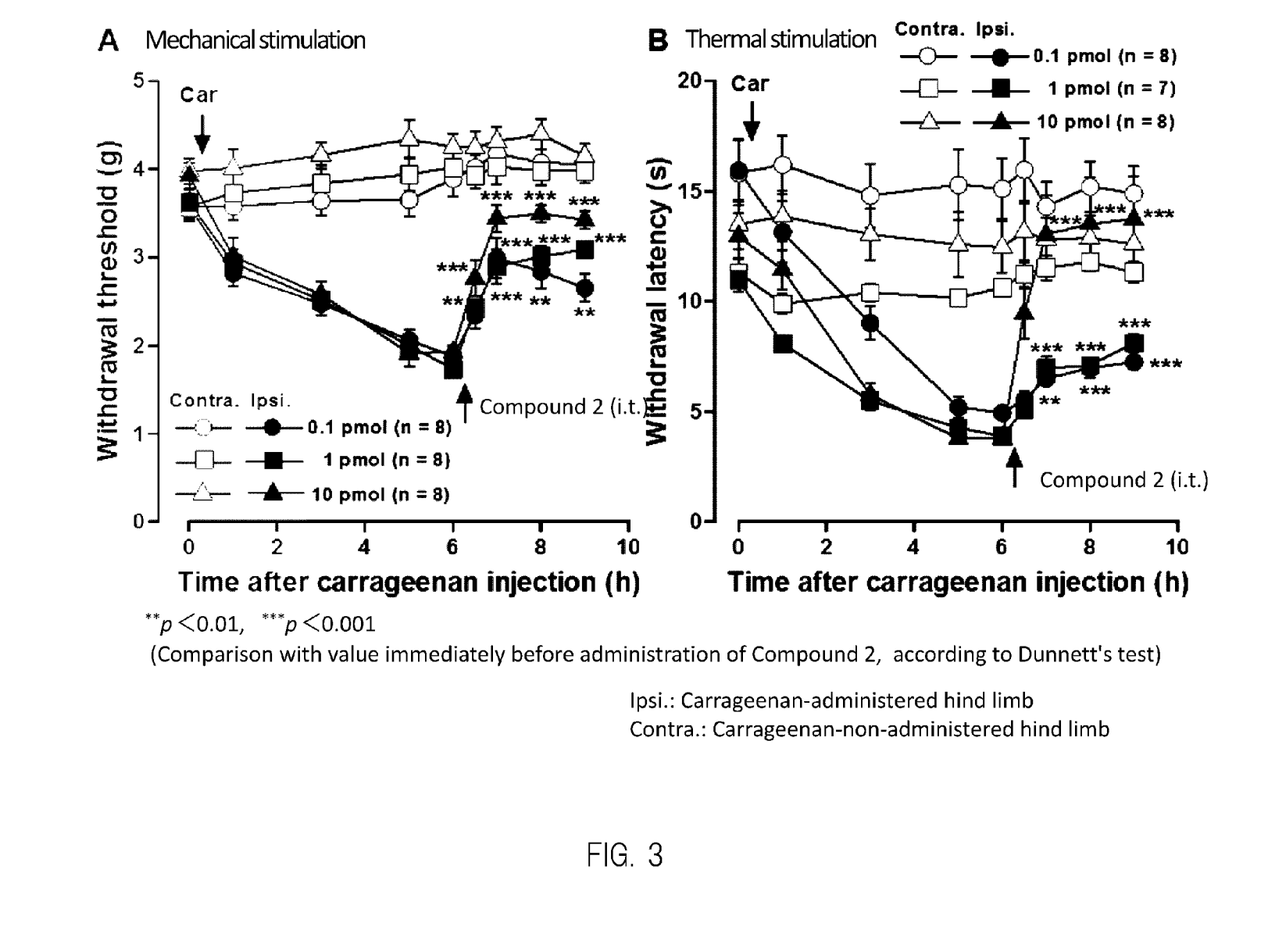
FIG. 3-is exemplary graphs illustrating effects of pain therapy with a compound 2 of carrageenan-induced inflammatory pain model mice. The compound 2 was administered intrathecally, and reactions to mechanical stimulation and thermal stimulation were examined. A of FIG. 3 illustrates exemplary results of examination regarding threshold of a withdrawal reflex behavior to mechanical stimulation, and B of FIG. 3 illustrates exemplary results of examination regarding latency with respect to thermal stimulation.

Before and after carrageenan (2%, 25 µl) was subcutaneously administered to a one-side hind limb sole of each mouse (male, C57BL/6J, 6 to 8 weeks old), mechanical stimulation or thermal stimulation was applied, and threshold (mechanical stimulation) and latency (thermal stimulation) of a withdrawal reflex behavior of the hind limb were measured. The appearance of the phenomenon of mechanical allodynia or the appearance of thermal hyperalgesia due to carrageenan was checked over six hours after the administration, and thereafter, the compound 2 was administered intrathecally (0.1 pmol, 1 pmol, or 10 pmol). Effects were examined over three hours thereafter. The solution of the compound 2 was prepared by dissolving the compound 2 in 99% DMSO, and diluting the same with physiological saline solution (0.2% DMSO in physiological saline solution).

The results are illustrated in FIG. 3. A of FIG. 3 illustrates the results of examination on the threshold of the withdrawal reflex behavior with respect to the mechanical stimulation, and B of FIG. 3 illustrates the results of examination of the latency with respect to the thermal stimulation.

As illustrated in FIG. 3, pain was significantly reduced by the administration of the compound 2.

Experiment Example 4

Subcutaneous plantar administration of complete Freund's adjuvant (CFA) caused prolonged inflammation, which was more persistent than the inflammation caused in the carrageenan models, and this caused phenomena of hypersensitivity to mechanical stimulation and thermal stimulation. Using these CFA model mice, pain therapy effects of the compound 3 were evaluated. Before and after CFA (25 µl) was subcutaneously administered to a one-side hind limb sole of each mouse (male, C57BL/6J, 6 to 8 weeks old), mechanical stimulation was applied, and threshold of a withdrawal reflex behavior of the hind limb was measured. The appearance of the phenomenon of mechanical allodynia due to CFA was checked three days after the administration, and the compound 3 was administered intrathecally. Effects were examined over three hours thereafter. The solution of the compound 3 was prepared by dissolving the compound 3 in 99% DMSO, and diluting the same with physiological saline solution (0.2% DMSO in physiological saline solution). The results are illustrated in FIG. 4.

Figure 4:
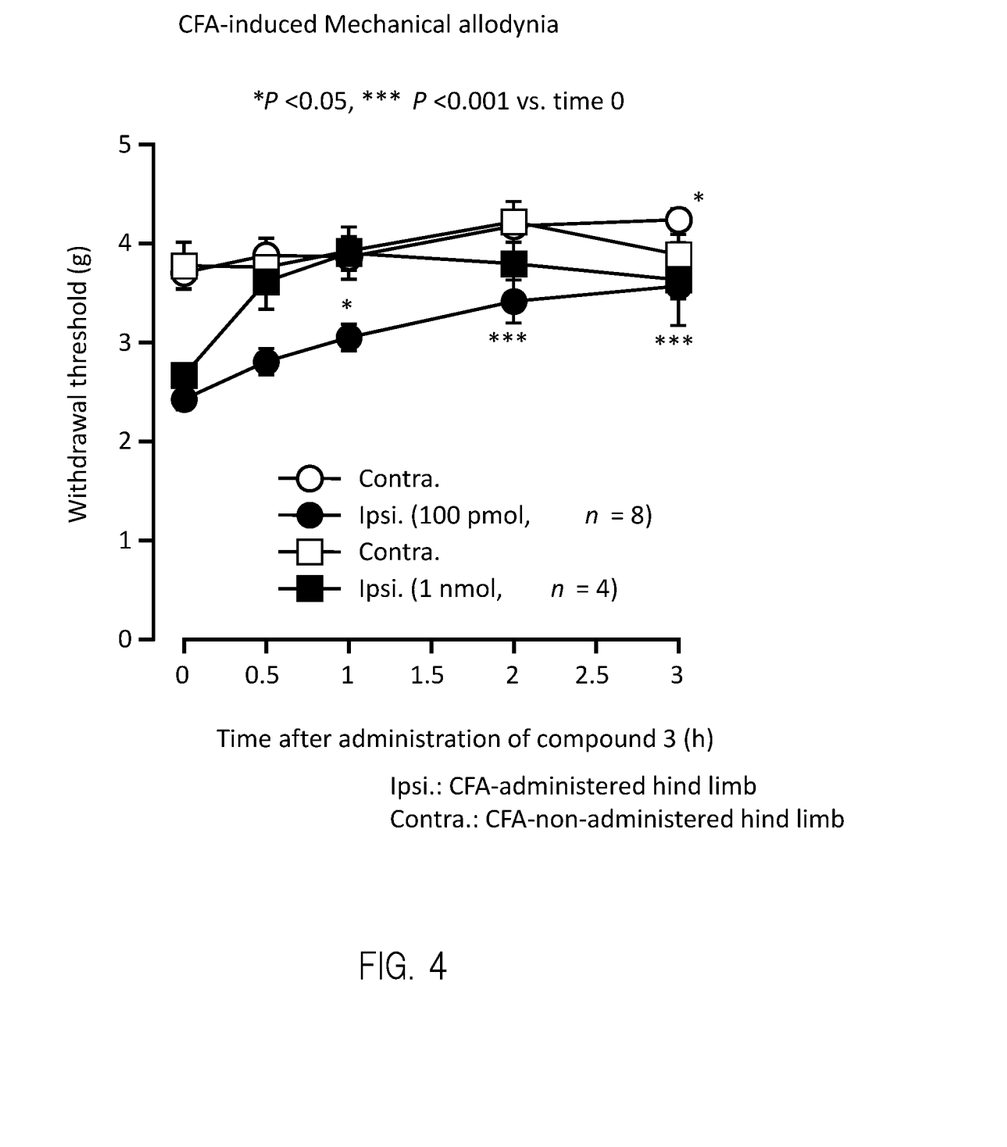
FIG. 4 is an exemplary graph illustrating effects of pain therapy with a compound 3 of complete Freund's adjuvant-induced inflammatory pain model mice. The compound 3 was administered intrathecally, and threshold of a withdrawal reflex behavior to mechanical stimulation was determined.

As illustrated in FIG. 4, pain was significantly suppressed by the administration of the compound 3.

Experiment Example 5

Before and after carrageenan (2%, 25 µl) was subcutaneously administered to a one-side hind limb sole of each mouse (male, C57BL/6J, 6 to 8 weeks old), mechanical stimulation or thermal stimulation was applied, and threshold (mechanical stimulation) and latency (thermal stimulation) of a withdrawal reflex behavior of the hind limb were measured. The appearance of the phenomenon of mechanical allodynia or the appearance of the thermal hyperalgesia due to carrageenan was checked over six hours after the administration, and thereafter, the compound 4 was administered intrathecally. Effects were examined over three hours thereafter. The solution of the compound 4 was prepared by dissolving the compound 2 in 99% DMSO, and diluting the same with physiological saline solution (0.2% DMSO in physiological saline solution). The results are illustrated in FIG. 5.

Figure 5:
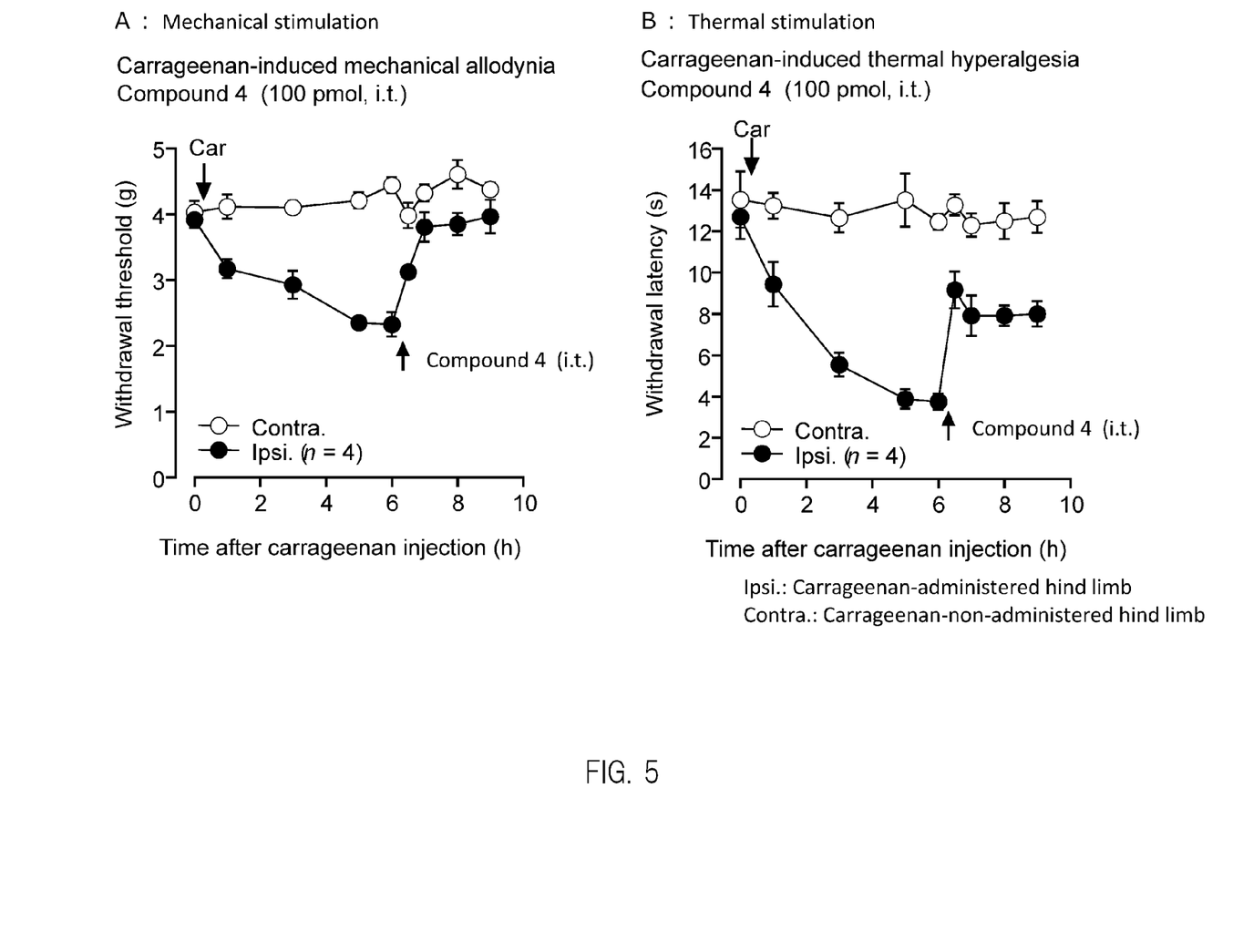
FIG. 5 is an exemplary graphs illustrating effects of pain therapy with a compound 4 of carrageenan-induced inflammatory pain model mice. The compound 4 was administered intrathecally, and reactions to mechanical stimulation and thermal stimulation were examined. A of FIG. 5 illustrates exemplary results of examination regarding threshold of a withdrawal reflex behavior to mechanical stimulation, and B of FIG. 5 illustrates exemplary results of examination regarding latency with respect to thermal stimulation.

As illustrated in FIG. 5, pain was significantly suppressed by the administration of the compound 4.

Compound 4

Experiment Example 6

Before and after carrageenan (2%, 25 µl) was subcutaneously administered to a one-side hind limb sole of each mouse (male, C57BL/6J, 6 to 8 weeks old), thermal stimulation was applied, and latency of a withdrawal reflex behavior of the hind limb was measured. The appearance of the phenomenon of thermal hyperalgesia due to carrageenan was checked over six hours after the administration, and thereafter, the compound 5 was administered intrathecally. Effects were examined over three hours thereafter. The solution of the compound 5 was prepared by dissolving the compound 5 in 99% DMSO, and diluting the same with physiological saline solution (0.2% DMSO in physiological saline solution). The results are illustrated in FIG. 6.

Figure 6:
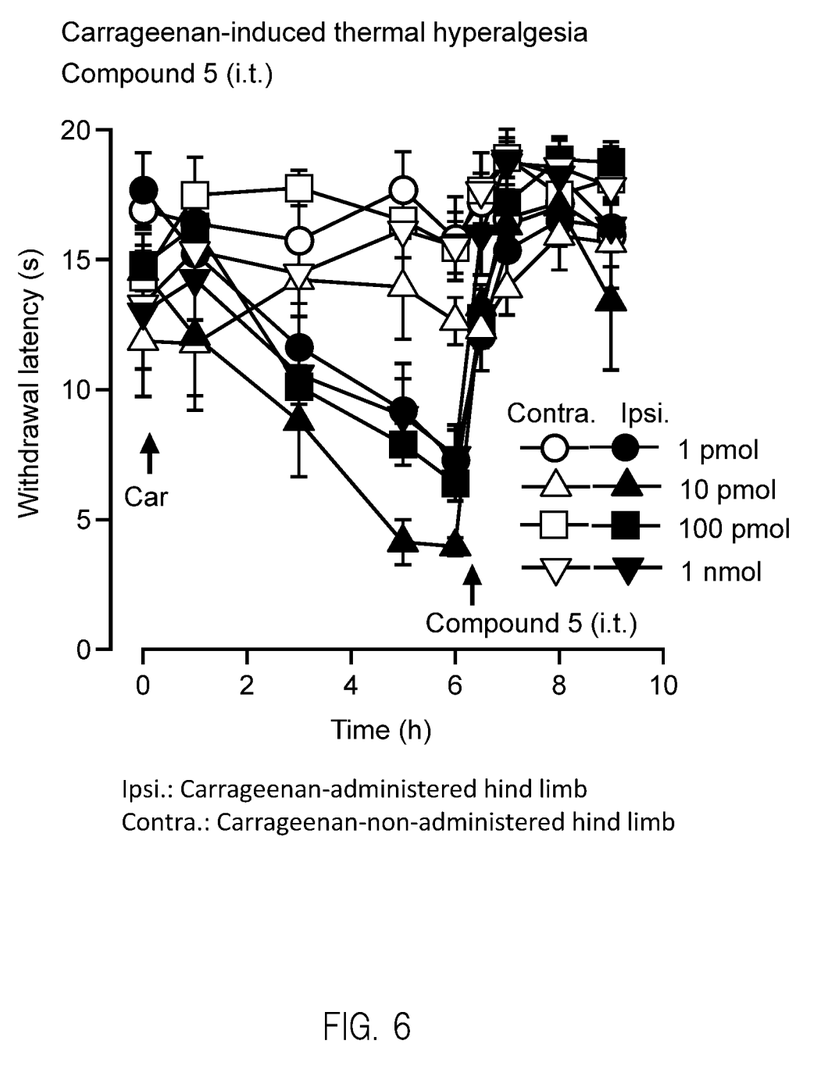
FIG. 6 is an exemplary graph illustrating effects of pain therapy with a compound 5 of carrageenan-induced inflammatory pain model mice. The compound 5 was administered intrathecally, and latency (time) until a withdrawal reflex behavior to thermal stimulation was determined.

As illustrated in FIG. 6, pain was significantly suppressed by the administration of the compound 5.

Experiment Example 7

Before and after carrageenan (2%, 25 µl) was subcutaneously administered to a one-side hind limb sole of each mouse (male, C57BL/6J, 6 to 8 weeks old), thermal stimulation was applied, and latency of a withdrawal reflex behavior of the hind limb was measured. The appearance of the phenomenon of thermal hyperalgesia due to carrageenan was checked over six hours after the administration, and thereafter, the compound 6 was administered intrathecally. Effects were examined over three hours thereafter. The solution of the compound 6 was prepared by dissolving the compound 6 in 99% DMSO, and diluting the same with physiological saline solution (0.2% DMSO in physiological saline solution). The results are illustrated in FIG. 7.

Figure 7:
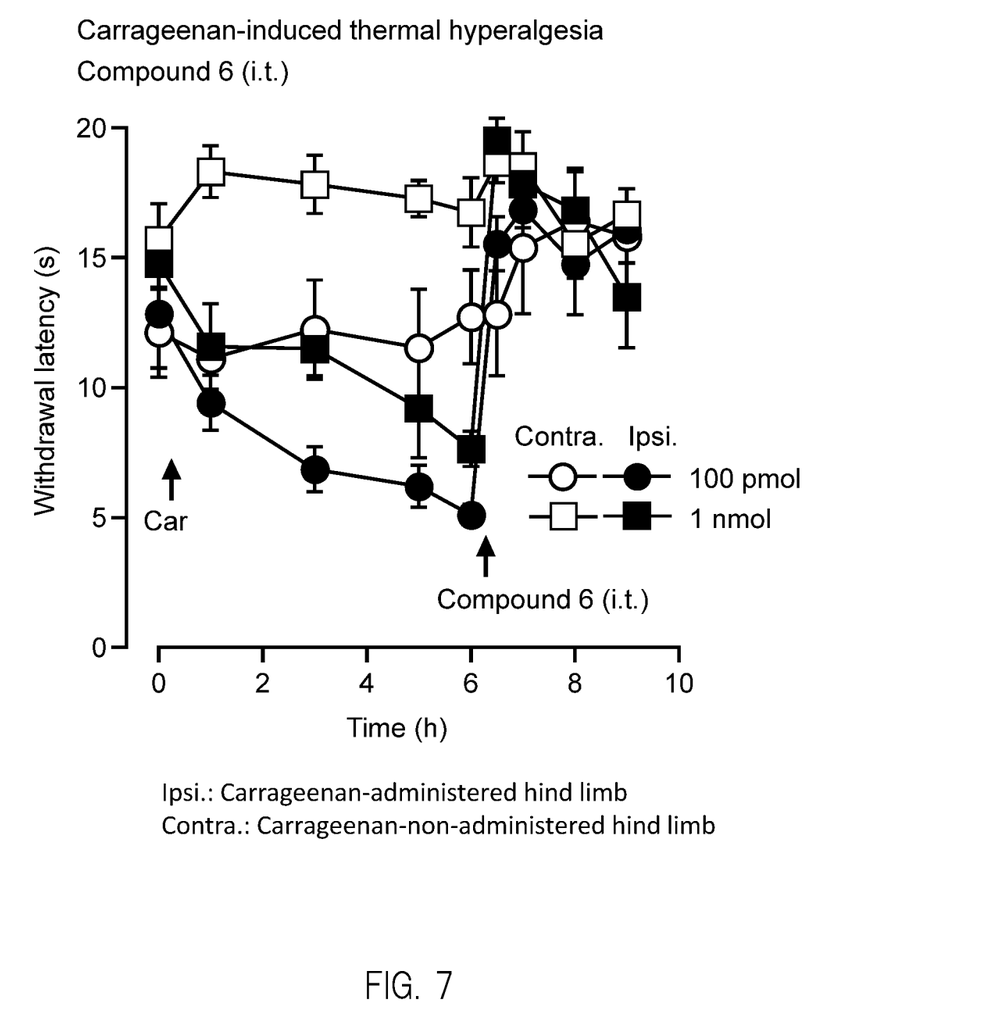
FIG. 7 is an exemplary graph illustrating effects of pain therapy with a compound 6 of carrageenan-induced inflammatory pain model mice. The compound 6 was administered intrathecally, and latency (time) until a withdrawal reflex behavior to thermal stimulation was determined.

As illustrated in FIG. 7, pain was significantly suppressed by the administration of the compound 6.

Experiment Example 8

Carrageenan was subcutaneously injected to a hind limb sole of each mouse, and seven hours later, the compound 1 and an opioid antagonist were simultaneously administered intraperitoneally. At one hour after the administration and at three hours after the administration, therapeutic effects with respect to mechanical allodynia were evaluated. Specific conditions were as follows.

Mouse: C57B116J, male, 8 weeks old

Induction of pain: Pain was induced by subcutaneously injecting 20 µL of physiological saline solution containing 2% λ-carrageenan to a hind limb sole.

Administration of therapeutic agent: 1% Tween80 (trademark) physiological saline solution containing 2% DMSO in which the compound 1 and an opioid antagonist described below were dissolved was administered intraperitoneally, in an amount of 0.01 mL per 1 g of the body weight (about 0.2 mL of the solution was administered per one mouse). The compound 1 was prepared so as to be 1 nmol per 1 g of the body weight of the mouse. The opioid antagonist was prepared so as to be 20 nmol per 1g of the body weight of the mouse.

Opioid antagonist MNTX: Methylnaltrexone bromide Antagonist selective to a ropioid receptor and a ic-opioid receptor. Unable to pass through the blood-brain barrier.

Opioid antagonist NAL-M: Naloxone methioclide Antagonist not selective to an opioid receptor. Unable to pass through the blood-brain barrier.

Evaluation of pain: Evaluation was performed by von Frey test, as is the case with the experiment example 1. The results are illustrated in FIG. 8.

Figure 8:
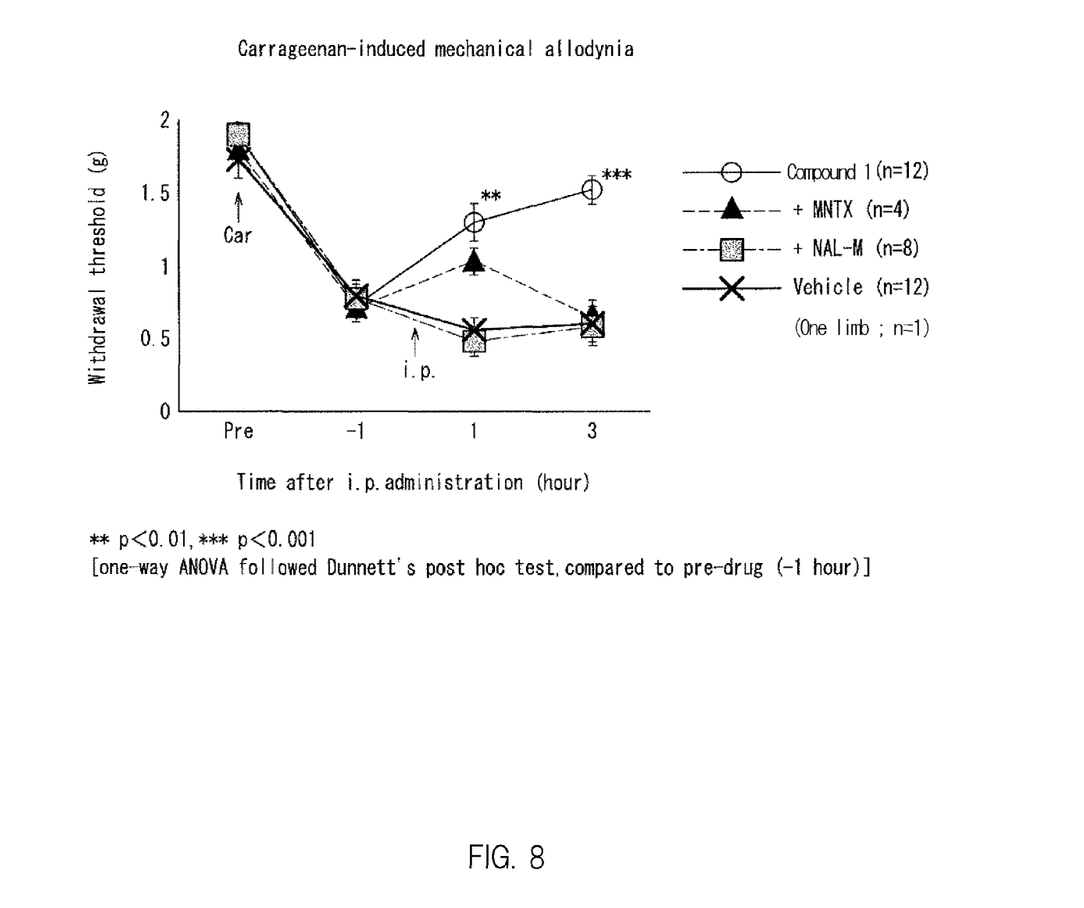
FIG. 8 is an exemplary graph illustrating evaluation of influences of the compound 1 and an opioid antagonist to effects of pain therapy when the compound 1 and the opioid antagonist were simultaneously administered to carrageenan-induced inflammatory pain model mice. The compound 1 and the opioid antagonist were administered intraperitoneally, and reactions to mechanical stimulation were examined.

As illustrated in FIG. 8, the effects of the analgesic action by the compound 1 were hindered by a peripheral opioid antagonist. It is therefore considered that the analgesic action by the compound 1 against pain was exerted via an opioid receptor.

The invention claimed is:

1. A method for reducing pain, suppressing the exacerbation of pain, or treating pain, wherein the pain is selected from an acute pain, an inflammatory pain, a visceralgia, a breakthrough pain, a nociceptive pain, a neuropathic pain, and a chronic pain, the method comprising administering a pharmaceutical composition containing as an active ingredient a compound of formula II wherein $X_1$ is halogen or a substituted or unsubstituted methyl group, $Y_1$ is halogen or a substituted or unsubstituted straight-chain or branched-chain or cyclic alkyl group having 1 to 6 carbon atoms, and $Z_1$ and $W_1$ each independently are hydrogen, halogen, hydroxyl, a straight-chain or branched-chain or cyclic alkoxy group having 1 to 6 carbon atoms, or a substituted or unsubstituted straight-chain or branched-chain or cyclic alkyl group having 1 to 6 carbon atoms, or a pharmaceutically permissible salt thereof, to a target that requires the administration of the pharmaceutical composition, wherein the target is a pain patient.

2. The method according to claim 1, wherein the pain is an inflammatory pain, and the target is an inflammatory pain patient.

3. The method according to claim 1, wherein $X_1$ is halogen or methyl.

4. The method according to claim 3, wherein $Y_1$ is a $C_{1-4}$ alkyl group.

5. The method according to claim 3, wherein the pain is a neuropathic pain, and the target is a neuropathic pain patient.

6. The method according to claim 1, wherein $X_1$ is methyl, $Y_1$ is ethyl, $Z_1$ is halogen or a $C_{1-4}$ alkoxy group, and $W_1$ is hydrogen.

7. The method according to claim 6, wherein the pain is an inflammatory pain, and the target is an inflammatory pain patient.

8. The method according to claim 6, wherein the pain is a neuropathic pain, and the target is a neuropathic pain patient.

9. The method according to claim 1, wherein the compound is a compound having one of the formulae below

-continued and

10. The method according to claim 2, wherein the compound is a compound having one of formulae below

-continued and

11. The method according to claim 10, wherein the pain is a neuropathic pain, and the target is a neuropathic pain patient.

* * * * *